United States Patent
Saeki

(10) Patent No.: US 10,154,827 B2
(45) Date of Patent: Dec. 18, 2018

(54) PROBE FOR ULTRASONIC DIAGNOSTIC EQUIPMENT

(71) Applicant: NIHON DEMPA KOGYO CO., LTD., Tokyo (JP)

(72) Inventor: Isao Saeki, Saitama (JP)

(73) Assignee: NIHON DEMPA KOGYO CO., LTD., Tokyo (JP)

(*) Notice: Subject to any disclaimer, the term of this patent is extended or adjusted under 35 U.S.C. 154(b) by 820 days.

(21) Appl. No.: 14/445,066

(22) Filed: Jul. 29, 2014

(65) Prior Publication Data

US 2015/0038848 A1    Feb. 5, 2015

(30) Foreign Application Priority Data

Jul. 30, 2013 (JP) ................... 2013-157286

(51) Int. Cl.
*A61B 8/00* (2006.01)
*A61B 8/12* (2006.01)

(52) U.S. Cl.
CPC .............. *A61B 8/4422* (2013.01); *A61B 8/12* (2013.01); *A61B 8/4455* (2013.01)

(58) Field of Classification Search
None
See application file for complete search history.

(56) References Cited

U.S. PATENT DOCUMENTS

| | | | |
|---|---|---|---|
| 8,819,893 B2 | 9/2014 | Shishido et al. | |
| 2006/0144611 A1* | 7/2006 | Chiu | H01R 9/03 174/74 R |
| 2007/0106158 A1* | 5/2007 | Madan | A61B 8/4455 600/459 |

(Continued)

FOREIGN PATENT DOCUMENTS

| | | |
|---|---|---|
| CN | 202568309 | 12/2012 |
| JP | 2002-299850 | 10/2002 |

(Continued)

OTHER PUBLICATIONS

"Office Action of Japan Counterpart Application", dated Feb. 6, 2017, p. 1-p. 3, in which the listed references were cited.

(Continued)

*Primary Examiner* — Michael Carey
*Assistant Examiner* — Farouk Bruce
(74) *Attorney, Agent, or Firm* — JCIPRNET

(57) ABSTRACT

A probe for ultrasonic diagnostic equipment includes a cable, a cable outer periphery holder, and a depressed cone shape component. The cable outer periphery holder includes a deformable convex cone shape portion and a supporting surface that holds an outer peripheral of the cable. The depressed cone shape component has a depressed cone shape portion and fits the convex cone shape portion. The cable outer periphery holder has a water proof structure configured to prevent invasion of liquid from a gap formed between the outer periphery of the cable and the supporting surface. The water proof structure is configured to have the convex cone shape portion and the depressed cone shape component to fit so as to deform the convex cone shape portion. The deformation forms a reduced diameter portion to eliminate the gap, the reduced diameter portion having a diameter.

4 Claims, 4 Drawing Sheets

(56) References Cited

U.S. PATENT DOCUMENTS

| | | | | |
|---|---|---|---|---|
| 2008/0233791 A1* | 9/2008 | Hanks | ............... | H01R 4/5033 |
| | | | | 439/427 |
| 2008/0255412 A1* | 10/2008 | Surti | ............... | A61B 17/12013 |
| | | | | 600/104 |
| 2008/0311790 A1* | 12/2008 | Malloy | ............... | H01R 13/622 |
| | | | | 439/583 |
| 2012/0037416 A1* | 2/2012 | Chiou | ............... | H02G 3/0658 |
| | | | | 174/652 |

FOREIGN PATENT DOCUMENTS

| | | |
|---|---|---|
| JP | 2005-245785 | 9/2005 |
| JP | 3163407 | 10/2010 |
| JP | 2012-034877 | 2/2012 |
| WO | 2013065598 | 5/2013 |

OTHER PUBLICATIONS

"Office Action of China Counterpart Application," with machine English translation thereof, dated Aug. 2, 2017, p. 1-p. 10, in which the listed references were cited.

\* cited by examiner

PROBE FOR ULTRASONIC DIAGNOSTIC EQUIPMENT

CROSS REFERENCE TO RELATED APPLICATIONS

This application claims the priority benefit of Japanese application serial no. 2013-157286, filed on Jul. 30, 2013. The entirety of the above-mentioned patent application is hereby incorporated by reference herein and made a part of specification.

FIELD

This disclosure relates to a probe for medical ultrasonic diagnostic equipment that obtains an image inside a living body using a ultrasonic sound wave, and especially relates to a structure that prevents invasion of liquid into the probe from a gap formed between a cable connecting the ultrasonic diagnostic equipment and the probe and a supporting member holding the outer peripheral portion of this cable.

DESCRIPTION OF THE RELATED ART

The probe having an ultrasonic transducer for the ultrasonic diagnostic equipment is always disinfected and cleaned after the ultrasonic wave diagnosis of a living body. Thus, the probe needs to have a water proof structure. However, the cable connecting the ultrasonic diagnostic equipment and the probe has a covering portion made of a flexible material such as silicon rubber. This brings a problem that it is very difficult to perfectly ensure the water proof structure of the portion connecting the cable and the probe.

Hence, so far, in order to ensure this type of water proof structure, an adhesive agent has been filled up and hardened in the gap between the aforementioned cable and a member holding the outer peripheral portion of this cable to prevent the invasion of liquid into the probe.

That is, as illustrated in FIG. 3 and FIG. 4, the conventional technique bonds the outer peripheral portion of a cable 11 with a soft synthetic resin coat 11a to the bore of a cable outer peripheral portion supporting member 12. Then, a lid member 13 is fixedly secured to a housing (externally-mounted case) 15 of a probe P by hardening the adhesive agent, and a metal fitting 14 made of a metal or a synthetic resin is screwed into a screw portion 16 formed on the inner peripheral portion of the lid member 13, so as to secure the cable outer peripheral portion supporting member 12 that holds the cable 11. This covers a liquid invasion path as illustrated in FIG. 4, preventing the invasion of liquid into the probe P.

However, in such the conventional method for preventing the liquid invasion, the necessary amount of adhesive agent needs to be filled up, applied over, and hardened in the gap each time, and in the case where the probe is disassembled for repair, a part of components fixedly secured by the adhesive agent needs to be broken. These present a problem such as significantly poor work efficiency and disassembly efficiency of the probe (see Japanese Unexamined Patent Application Publication Nos. 2002-299850 and 2005-245785).

A need thus exists for a probe for ultrasonic diagnostic equipment which is not susceptible to the drawback mentioned above.

SUMMARY

A probe for ultrasonic diagnostic equipment includes a cable, a cable outer periphery holder, and a depressed cone shape component. The cable is configured to connect ultrasonic diagnostic equipment and a probe having an ultrasonic transducer. The cable outer periphery holder includes a deformable convex cone shape portion. The cable outer periphery holder has a supporting surface. The supporting surface holds an outer peripheral of the cable. The depressed cone shape component has a depressed cone shape portion. The depressed cone shape component fits the convex cone shape portion. The cable outer periphery holder has a water proof structure configured to prevent invasion of liquid from a gap formed between the outer periphery of the cable and the supporting surface. The water proof structure is configured in a way that the convex cone shape portion and the depressed cone shape component are fit so as to deform the convex cone shape portion. The deformation forms a reduced diameter portion on the supporting surface with a diameter smaller than a diameter of another part of the supporting surface to eliminate the gap.

BRIEF DESCRIPTION OF THE DRAWINGS

The foregoing and additional features and characteristics of this disclosure will become more apparent from the following detailed description considered with reference to the accompanying drawings, wherein.

DETAILED DESCRIPTION

A description will be given of a water proof structure of a probe for ultrasonic diagnostic equipment according to embodiments of this disclosure based on the accompanying drawings.

Figure 1A:
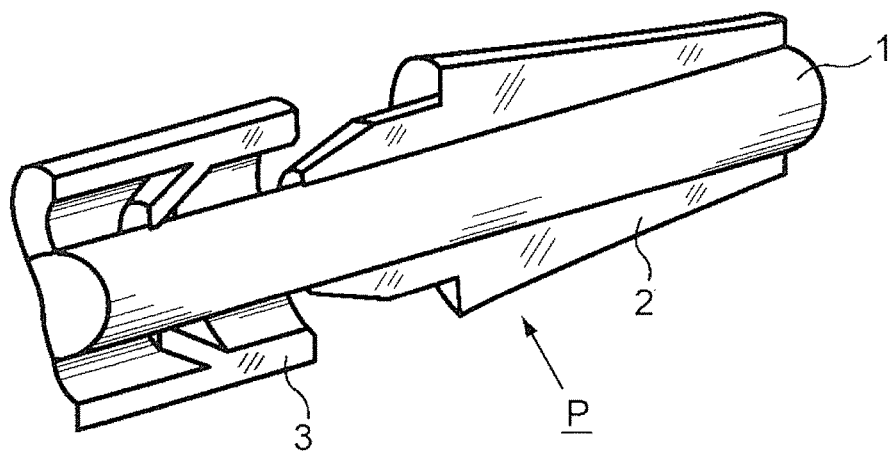
FIG. 1A is an exploded perspective view illustrating a water proof structure of a probe for ultrasonic diagnostic equipment according to a first embodiment of this disclosure.
Figure 1B:
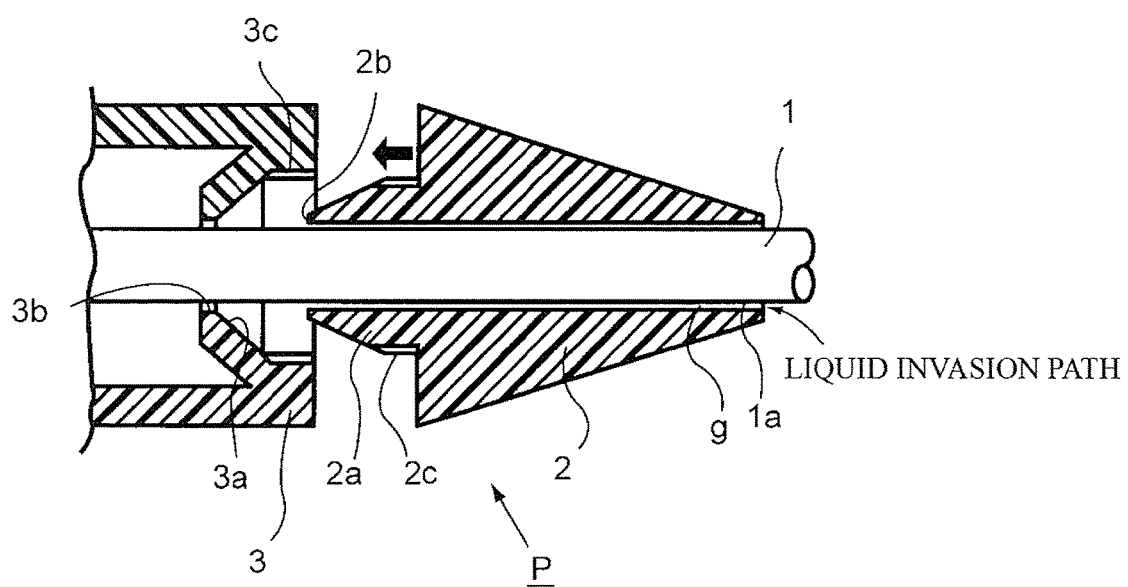
FIG. 1B is a partial cross-sectional view illustrating the water proof structure of the probe for ultrasonic diagnostic equipment according to the first embodiment.

As illustrated in FIGS. 1A and 1B, a water proof structure of a probe with an ultrasonic transducer of this disclosure functions to prevent liquid from invading through a liquid invasion path illustrated in FIG. 1B into a probe P. The liquid is assumed to invade from a gap "g" formed between a cable 1 (see FIGS. 1A and 1B), which has an outside portion coated with a soft synthetic resin and connects the ultrasonic diagnostic equipment (not shown) and the probe P, and a cable outer periphery holder 2 that holds this cable 1.

Specifically, the water proof structure for probe is constituted by forming a reduced diameter portion "s." The reduced diameter portion "s" is formed as described below. A cable outer periphery holder 2, which holds an outer periphery 1a of the cable 1 and is made of, for example, a flexible material such as silicon rubber, is formed to have a cross-sectional shape in a form of cone expanding toward the end. At an inlet side leading end 2b of the cable outer periphery holder 2, a convex cone shape portion 2a is formed. A depressed cone shape component 3, which is another component and is made of a material such as a hard synthetic resin, is formed to have a depressed cone shape portion 3a. Against this depressed cone shape portion 3a, the cable outer periphery holder 2 is pressed so that a male screw 2c in FIG. 2A formed at the base part of the convex cone shape portion 2a of the cable outer periphery holder 2 is pressed to a female screw 3c formed on the depressed cone shape component 3 in the arrow direction illustrated in FIG. 1B, while the convex cone shape portion 2a is press-fitted (fit) to the depressed cone shape portion 3a. This causes the leading end 2b of the flexible cable outer periphery holder 2 to deform in the radial direction so as to decrease the inside diameter of an opening portion of the leading end 2b, thus forming the reduced diameter portion "s. " This fastens the whole circumference of the outer periphery 1a of the cable 1 coated with a soft material and reduces the gap "g" in this part to seal, preventing the invasion of liquid from the outside of the probe P.

Embodiment 1

Figure 2A:
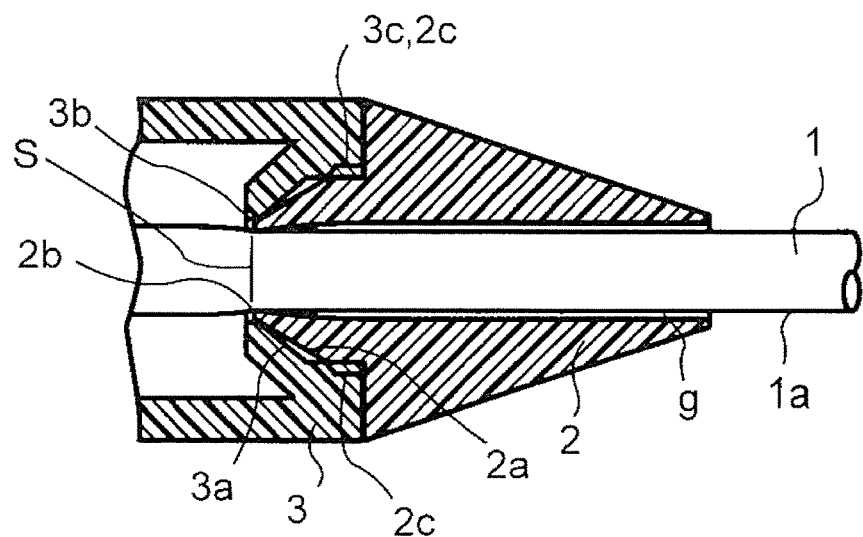
FIG. 2A is a sectional view illustrating the water proof structure of the probe according to the first embodiment where a convex cone shape of a cable outer periphery holder is pressed against an inner peripheral opening portion of a depressed cone shape component to form a reduced diameter portion so as to fasten a cable outer periphery.

According to Embodiment 1 of this disclosure, as illustrated in FIG. 2A, there is provided a water proof structure of the probe P for the ultrasonic diagnostic equipment. In the water proof structure, the cable outer periphery holder 2, which holds the outer periphery 1a of the cable 1 and is made of, for example, a flexible material such as silicon rubber, is formed to have a cross-sectional shape in a form of cone expanding toward the end. At the inlet side leading end 2b of the cable outer periphery holder 2, the convex cone shape portion 2a is formed. The depressed cone shape component 3, which is another component and is made of a material such as a hard synthetic resin, is formed to have the depressed cone shape portion 3a. Against this depressed cone shape portion 3a, the cable outer periphery holder 2 is pressed so that the male screw 2c formed at the base part of the convex cone shape portion 2a of the cable outer periphery holder 2 is threadably mounted on the female screw 3c formed on the depressed cone shape component 3.

Here, as illustrated in FIG. 2A, the convex cone shape portion 2a of the cable outer periphery holder 2 has an expanding corner formed to be smaller than that of the depressed cone shape component 3 and to exceed an opening portion 3b of the depressed cone shape component 3. This allows the leading end 2b to be in line contact with the depressed cone shape surface of the convex cone shape portion 2a, deforming the leading end 2b in the radial direction.

Hence, an opening portion of the leading end 2b of the flexible cable outer periphery holder 2 is deformed so as to decrease the inside diameter in the radial direction. This fastens the whole circumference of the outer periphery 1a of the cable 1 coated with a soft material, forms a reduced diameter portion "s," and reduces the gap "g" in this part to seal, preventing the invasion of liquid from the outside of the probe P.

Embodiment 2

Figure 2B:
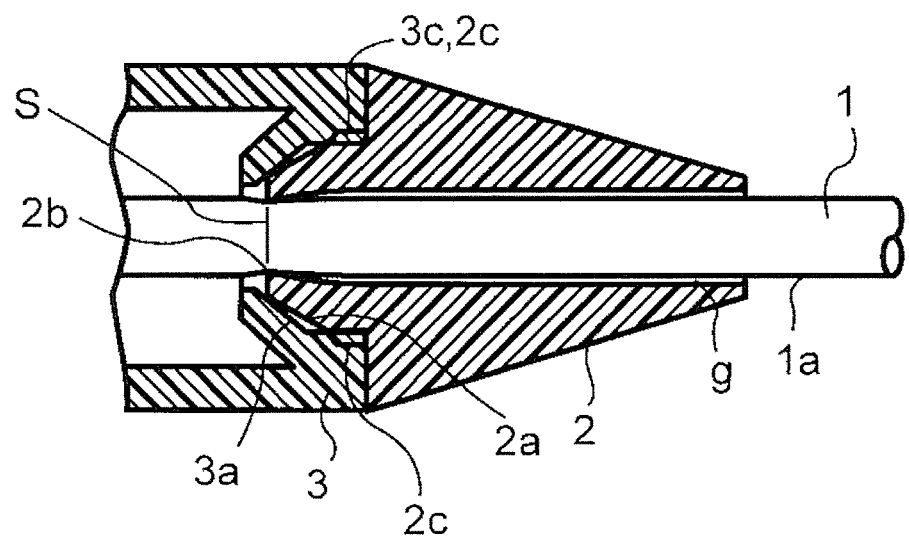
FIG. 2B is a sectional view illustrating a water proof structure of a probe according to a second embodiment where a convex cone shape of a cable outer periphery holder is in contact with an inclined surface of a depressed cone shape of a depressed cone shape component to form a reduced diameter portion so as to fasten a cable outer periphery.

According to Embodiment 2 of this disclosure, as illustrated in FIG. 2B, there is provided a water proof structure of the probe P for the ultrasonic diagnostic equipment. In the water proof structure, the cable outer periphery holder 2, which holds the outer periphery 1a of the cable 1 and is made of for example a flexible material such as silicon rubber, is formed to have a cross-sectional shape in a form of cone expanding toward the end. At the inlet side leading end 2b of the cable outer periphery holder 2, the convex cone shape portion 2a is formed. The depressed cone shape component 3, which is another component and is made of a material such as a hard synthetic resin, is formed to have the depressed cone shape portion 3a. Against this depressed cone shape portion 3a, the cable outer periphery holder 2 is pressed so that the male screw 2c formed at the base part of the convex cone shape portion 2a of the cable outer periphery holder 2 is threadably mounted on the female screw 3c formed on the depressed cone shape component 3.

Here, as illustrated in FIG. 2B, the convex cone shape portion 2a of the cable outer periphery holder 2 has the expanding corner formed to be smaller than that of the depressed cone shape component 3 and to reach the near side of the opening portion 3b of the depressed cone shape component 3. This allows the leading end 2b to be in line contact with an inclined surface of the depressed cone shape of the convex cone shape portion 2a, deforming the leading end 2b in the radial direction. Hence, the opening portion of the leading end 2b of the flexible cable outer periphery holder 2 is deformed so as to decrease the inside diameter in the radial direction. This fastens the whole circumference of the outer periphery 1 a of the cable 1 coated with a soft material, forms the reduced diameter portion "s," and reduces the gap "g" in this part to seal, preventing the invasion of liquid from the outside of the probe P.

Embodiment 3

Figure 2C:
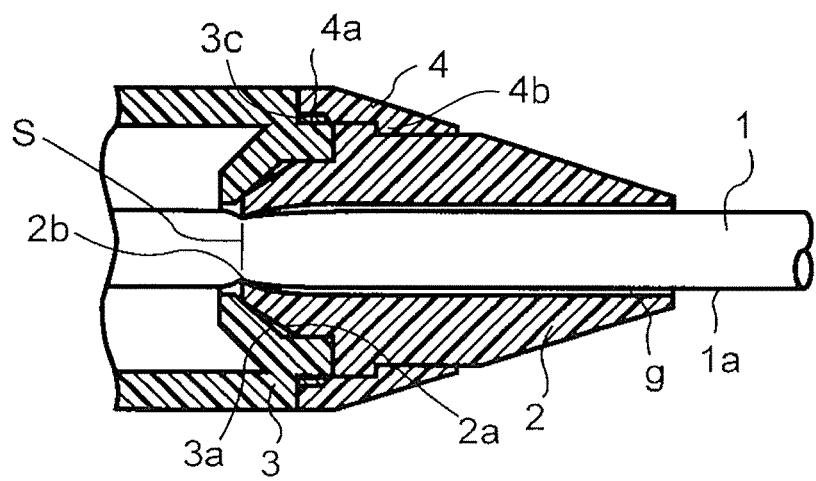
FIG. 2C is a sectional view illustrating a water proof structure of a probe according to yet another embodiment where a screwing component is separately disposed on the cable outer periphery holder.
Figure 3:
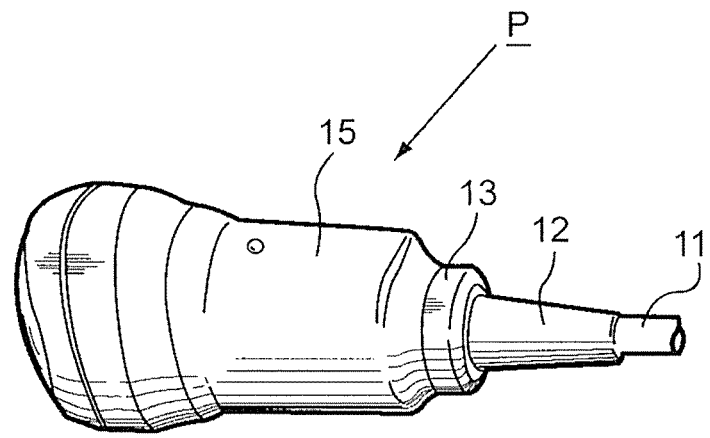
FIG. 3 is a perspective view illustrating an outside appearance of a conventional probe for an ultrasonic sound wave diagnosis transducer.
Figure 4:
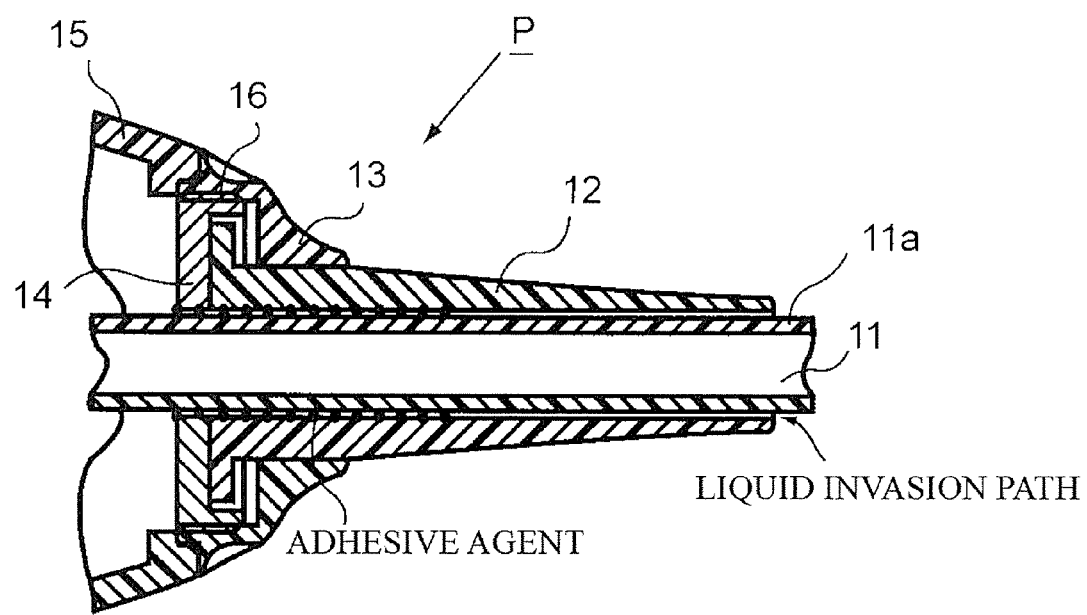
FIG. 4 is a partial sectional view illustrating the water proof structure of the probe indicated in FIG. 3.

According to Embodiment 3 of this disclosure, as illustrated in FIG. 2C, there is provided a water proof structure of the probe P for the ultrasonic diagnostic equipment. In the water proof structure, the cable outer periphery holder 2, which holds the outer periphery 1a of the cable 1 and is made of, for example, a flexible material such as silicon rubber, is formed to have a cross-sectional shape in a form of cone expanding toward the end. At the inlet side leading end 2b of the cable outer periphery holder 2, the convex cone shape portion 2a is formed. The depressed cone shape component 3, which is another component and is made of a material such as a hard synthetic resin, is formed to have the depressed cone shape portion 3a. Against this depressed cone shape portion 3a, the cable outer periphery holder 2 is pressed by a step potion 4b of an additionally-disposed screwing component 4 so that a female screw 4a formed on the additionally-disposed screwing component 4 is threadably mounted on a male screw 3c formed at the end portion of the depressed cone shape component 3.

Here, as illustrated in FIG. 2C, the convex cone shape portion 2a of the cable outer periphery holder 2 has the expanding corner formed to be smaller than that of the depressed cone shape component 3 and to reach the near side of the opening portion 3b of the depressed cone shape component 3. This allows the leading end 2b to be in line contact with the inclined surface of the depressed cone shape of the convex cone shape portion 2a, deforming the leading end 2b in the radial direction. Hence, the opening portion of the leading end 2b of the flexible cable outer periphery holder 2 is deformed so as to decrease the inside diameter in the radial direction. This fastens the whole circumference of the outer periphery 1a of the cable 1 coated with a soft material, forms the reduced diameter portion "s," and reduces the gap "g" in this part to seal, preventing the invasion of liquid from the outside of the probe P.

In this disclosure, means to press the convex cone shape portion to the depressed cone shape portion so as to fasten the cable outer periphery may be configured by threadably mounting a male screw and a female screw. The convex cone shape portion has the male screw. The female screw is formed at an opening end of the depressed cone shape component.

Further, in this disclosure, means to press the convex cone shape portion to the depressed cone shape portion so as to fasten the cable outer periphery may be configured by threadably mounting a female screw and a male screw. The female screw is formed at a screwing component fixedly secured to the convex cone shape portion. The male screw is formed at an opening end of the depressed cone shape component.

This disclosure can deform a holding portion of a flexible cable outer periphery holder so as to decrease the inside diameter of the holding portion, reducing the gap. Thus, the invasion of liquid into the probe can be prevented without using the adhesive agent.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A probe for ultrasonic diagnostic equipment, comprising:
    a cable configured to connect ultrasonic diagnostic equipment;
    a cable outer periphery holder that includes a deformable convex cone shape portion, the cable outer periphery holder having a supporting surface, the supporting surface holding an outer peripheral of the cable;
    a depressed cone that has a depressed cone shape portion and a side, the depressed cone fitting the convex cone shape portion, wherein the cable outer periphery holder has a water proof structure configured to prevent invasion of liquid from a gap formed between the outer periphery of the cable and the supporting surface; and
    a threadable mount that includes a female screw and a step portion, the step portion restraining the cable outer periphery holder to the depressed cone side, wherein the convex cone shape portion and the depressed cone are fastened by a threadable mounting, wherein the depressed cone has a male screw, and the threadable mounting is constituted of the male screw and the female screw, and
    wherein the water proof structure is configured in a way that the step portion presses the cable outer periphery holder toward the depressed cone side by the threadable mounting so that the convex cone shape portion and the depressed cone are fastened, and the convex cone shape portion is deformed by the depressed cone, the deformation forming a reduced diameter portion on one part of the supporting surface with a diameter smaller than a diameter of another part of the supporting surface to eliminate the gap.

2. The probe for ultrasonic diagnostic equipment according to claim 1, wherein the cable outer periphery holder is made of rubber.

3. The probe for ultrasonic diagnostic equipment according to claim 2, wherein
    the depressed cone shape portion has a diameter that becomes smaller as it gets away from a leading end of the cable outer periphery holder, and fastening an outer shape of the convex cone shape portion by the fitting between the convex cone shape portion and the depressed cone reduces an inside diameter of the convex cone shape portion, thereby eliminating the gap.

4. The probe for ultrasonic diagnostic equipment according to claim 1, wherein
    the depressed cone shape portion has a diameter that becomes smaller as it gets away from a leading end of the cable outer periphery holder, and fastening an outer shape of the convex cone shape portion by the fitting between the convex cone shape portion and the depressed cone reduces an inside diameter of the convex cone shape portion, thereby eliminating the gap.

* * * * *